United States Patent [19]

Paradies

[11] Patent Number: 5,434,302
[45] Date of Patent: Jul. 18, 1995

[54] METHOD FOR THE PREPARATION OF OPTICALLY ACTIVE 2-ARYL ALKYL ALDEHYDES AND FORMATION OF 2-ARYL-ALKANOIC ACIDS THEREFROM

[76] Inventor: H. Henrich Paradies, Goerresstrabe 38, Iserlon, D-5860, Germany

[21] Appl. No.: 198,600

[22] Filed: Feb. 18, 1994

[51] Int. Cl.$^6$ ............................................. C07C 51/29
[52] U.S. Cl. ...................... 562/419; 562/418; 564/276; 564/336; 568/433; 568/436; 560/56; 560/59; 560/61; 560/75; 560/102; 560/105
[58] Field of Search ................ 562/419, 418; 568/433, 568/436; 560/56, 59, 61, 75, 102, 105

[56] References Cited

U.S. PATENT DOCUMENTS

| | | |
|---|---|---|
| 3,228,831 | 1/1966 | Nicholson et al. |
| 3,927,084 | 12/1975 | Kogure et al. |
| 3,965,161 | 6/1976 | Kogure et al. |
| 4,209,638 | 6/1980 | Nicholson et al. |
| 4,381,313 | 4/1983 | Heusser et al. |
| 4,395,571 | 7/1983 | Dvorak ............................. 562/466 |

FOREIGN PATENT DOCUMENTS

| | | |
|---|---|---|
| 158913 | 10/1985 | European Pat. Off. |
| 195717 | 9/1986 | European Pat. Off. |
| 205215 | 12/1986 | European Pat. Off. |
| 407491 | 4/1965 | Japan |
| 504040 | 1/1975 | Japan |
| 1480971 | 3/1965 | United Kingdom |
| 2160866 | 1/1986 | United Kingdom |

OTHER PUBLICATIONS

Tamio Hayashi, *J. Org. Chem.*, 1983, 48, pp. 2195–2202.
Gottfried Blaschke, "Chromatographic Resolutions of Racemates", *Angew. Chem. Int. Ed. Engl.*, 1980, pp. 13–21.
Hutt, et al., J. Pharm. Pharmacol., 1983, 35, 693–704.
Piccilo, et al., J. Org. Chem., 1985, 50, 3945–3946.
Chemical Abstracts 1983 98:143138K.
Chemical Abstracts 1979 91:20125b.
Chemical Abstracts 1982 96:68650z.
Chemical Abstracts 1979 90:168303h.
Chemical Abstracts 1978, 89 23975y.
Chemical Abstracts 1978 88:104920h.
Hayashi, Asymmetric Reactions and Processes in Chemistry, 1982, 177–186.
Chemical Abstracts 1983 98:178945y.
Hayashi, et al., J. Org. Chem., 1983, 48, 2197–220.
Rieu, et al., Tetrahedron Report, 1986, 205, 4095–4131.
Noyori, et al., JACS, 1979, 101, 3129–3131.
Chemical Abstracts 88:50512f (1978).
Kobler, et al., Liebig's Ann. Chem., 1978, 1946–1962 with translation.
Foulkes and Hutton, Synthetic Communications, 1979, 9(7), 625–630.
Yamaguchi, et al., JACS, 1972, 94(26), 9254–9255.
Larsen, et al., JACS, 1989, 111, 7650–7651.
Corey, et al., JACS, 1987, 109, 5551–5553.
Chemical Abstracts 1980 92:6253F.
Paradies, et al., Pharmaceutical Manufacturing, 171–174, 1991.

*Primary Examiner*—Michael L. Shippen
*Attorney, Agent, or Firm*—Scully, Scott, Murphy & Presser

[57] ABSTRACT

The present process is directed to preparing optically active 2-aryl alkyl aldehydes by various processes through the use of an optically active amine, (−)-2′-amino-3-phenyl propane. The aldehyde formed can then be oxidized to produce the corresponding acid.

37 Claims, No Drawings

5,434,302

METHOD FOR THE PREPARATION OF OPTICALLY ACTIVE 2-ARYL ALKYL ALDEHYDES AND FORMATION OF 2-ARYL-ALKANOIC ACIDS THEREFROM

FIELD OF THE INVENTION

The present invention relates to a process for preparing optically active 2-aryl-alkyl aldehydes. These alkyl aldehydes are prepared by reacting a 2-aryl alkanal with a derivative of (S)-(−)2-amino-3-phenyl propane and treating the product thereof with a lithium base in the presence of molecular sieves or a drying agent, followed by treatment with alkyl halides and subsequent protonation. The chiral aldehyde formed the present process is an intermediate in the formation of the corresponding 2-aryl propionic acid and can be converted to the same via oxidation.

BACKGROUND OF THE INVENTION

The 2-aryl propionic acids are an important subclass of non-steroidal anti-inflammatory compounds having high analgesic properties. These compounds have been shown to be effective against pain and inflammatory action. In addition, some of the 2-aryl-propionic acids have been shown to possess non-steroidal anti-inflammatory activity and possess mechanism of action beyond the classical cyclooxygenase pathway inhibition.

Many of the 2-aryl propionic acids, such as, ibuprofen and kekoprofen, exists as racemates. See F. Jamali, *European. Journal. Drug. Metab. Pharmacokinet.*, 1988, 13, 1–9; Hurt, et al., in *J. Pharm. Pharmacol.*, 1983, 35, 693–704; and Jamali, et al. in *J. Pharm. Sci.*, 1989, 78, 695–715.

It has been shown that with respect to the 2-aryl propionic acids that exist as enantiomers, the more active form is the S-enantiomer, while the R-enantiomer is either inactive or has reduced activity. Furthermore, with respect to the efficacy of the R-enantiomer of the 2-aryl propionic acid, it has been suggested that its activity is due in part to an in vivo inversion of the R-stereoisomers to the active Senantiomer. However, in vivo and in vitro investigations clearly show that the S-enantiomeric form is the more pharmacologically active stereoisomer.

Thus, the S-enantiomer is the more desired stereoisomer. The S-enantiomer has several therapeutic advantages. For example, less S-enantiomer is required than the corresponding racemic or the R-enantiomer to achieve a desired biological effect. Consequently, in order to achieve an efficacious response, less S-stereoisomer relative to the corresponding R-enantiomer or racemic mixture needs to be administered. Furthermore, the skilled artisan would expect less side effects using the S-enantiomers than with the racemic mixture or with the R-isomer. Finally, drug action of the S-enantiomer is faster then with the racemic mixture since the receptors are enantiospecific having a high intrinsic infinity for the S-enantiomeric molecules.

Therefore, it is desirable to have a preparation of S-enantiomers of the 2 aryl-propionic acid with high optical purity that can be produced in an efficient manner. At present, only a few methods for a stereospecific chemical synthesis for 2 aryl propionic acids are known for industrial application. While many approaches have been developed, the majority of them lack simplicity and high stereoselectivity. See for example, Luball, et al., *JACS*, 1988, 110, 7447; Kagan, et al. in "New Approaches in Asymmetric Synthesis" in *Topics in Stereochemistry*. For example, α-hydroxy esters as the chiral agents (Lassen, in *JACS*, 1989, 111, 670–7691) or asymmetric ketones, Paradies, et al. in *Pharmaceutical Manufacturing*, 1991, 192–196, as the chiral agents have been utilized in stereospecific synthesis.

Optically active alpha-alkyl-aldehydes have been prepared through the intermediacy of an imine or a hydrazone. See, for example, Bergbreiter, et al., 1983, "Alkylation of Imine and Amine Salts", in *Asymmetric Synthesis*, editor J. D. Morrison, Orlando, Fla., Academic Press, Vol. 2A, page 243; D. Enders, "Alkylation of Chiral Hydrazones" in *Asymmetric Synthesis*, Ed. J. D. Morrison, Orlando, Fla., Academic Press, Volume 30, page 275; and Meyers, et al. in *J. Org. Chem.* 1978, 43, 892.

However, the present process provides an inexpensive and facile synthetic route for the preparation of S-aryl propionic acids in high enantiomeric excess. The key to the synthetic route of optically pure enantiomers of 2-aryl alkanoic acids, especially S or R- arylpropionic acids, is the formation of the corresponding 2-aryl-alkyl aldehyde which can be easily oxidized to the 2-aryl propionic acid. The aldehyde formed in accordance with the present invention is optically active and formed in enantiomeric excess and is prepared using relatively inexpensive and readily available starting materials as described herein. By using the present process, the enantiomers of 2-aryl alkyl aldehydes and 2-aryl alkanoic acids are formed in high chemical yields and both can be formed in the S-configuration with greater than 95% optical purity.

BRIEF SUMMARY OF THE INVENTION

The present invention relates to a method for preparing a stereospecific chemical synthesis of optically pure enantiomers of 2-aryl alkyl aldehydes having the formula

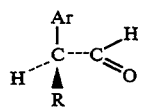

which comprises reacting an α-aryl substituted aliphatic aldehyde of the formula:

with an optically active amine of the formula

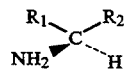

and treating the aldimine formed therefrom with a lithium containing base to produce a lithio-enanime, then reacting said lithio-enanime with an alkyl halide to produce a compound having the formula:

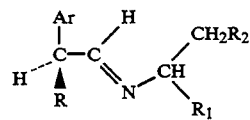

and hydrolyzing this compound to form said aldehyde, wherein

Ar is aryl or substituted aryl, R is lower alkyl, $R_1$ is aryl lower alkyl or substituted aryl lower alkyl and $R_2$ is lower alkoxy lower alkylene. The present invention is also directed to preparing an optically active 2-aryl-alkanoic acid which comprises forming the optically active aldehyde described hereinabove in accordance with the procedure described herein and oxidizing said optically active aldehyde to form the optically active 2-aryl-alkanoic acid.

DETAILED DESCRIPTION OF THE INVENTION

As described hereinabove, the present invention is directed to a process for preparing an optically active aldehyde which can then be used to prepare the corresponding optically active alkanoic acid.

As used herein lower alkyl, used alone or in combination, refers to an alkyl group containing 1 to 20 carbon atoms. These alkyl groups maybe straight-chained or branched and include such groups as methyl, ethyl, propyl, isopropyl, butyl, isobutyl, secondary butyl, tertiary butyl, n-pentyl, isopentyl, neopentyl, hexyl, heptyl, octyl, 2-ethylhexyl, 1,1,3,3-tetramethylbutyl, nonyl, decyl, dodecyl, tetradecyl, pentadecyl, hexadecyl, octadecyl, eicosyl, and the like. It is more preferred that the alkyl groups contain 1-6 carbon atoms. Even more preferred alkyl groups contain 1-3 carbon atoms and the most preferred alkyl group is methyl.

An alkylene group, as defined herein, is an bridging alkyl group, as defined herein. Examples include methylene, ethylene, and the like.

The alkoxy group, used alone or in combination, is an alkyl group which is attached to the principal chain by an oxygen atom. Examples include methoxy, ethoxy, propoxy, butoxy, isobutoxy, tertbutoxy and the like.

Alkoxyalkylene, as used herein, is an alkoxy group attached to a bridging alkylene group which in turn is attached to the principal chain. Both the alkoxy moiety and the alkylene moiety of said alkoxy alkylene may be straight chained or branched. It is preferred that the alkoxy moiety is straight chained, and it is also preferred that the alkylene moiety is straight chained, and it is most preferred that both the alkoxy moiety and the alkylene moiety are straight chained. The alkoxy alkylene may contain from 1 to 20 carbon atoms, but it is preferred that it contains 1-8 carbon atoms. Examples include methoxymethylene, ethoxy-methylene, propoxymethylene, isopropoxymethylene, butoxymethylene, isobutoxymethylene, tertiary butoxymethylene, pentyloxymethylene, hexyloxymethylene, heptyloxymethylene, octyloxymethylene, 2-methoxyethylene, 2-ethoxyethylene, 2-propoxyethylene, 2-butoxyethylene, 2-hexyloxyethylene, 2-octyloxyethylene, 3-methoxypropylene, 3-ethoxypropylene, 3-propoxypropylene, 3-butoxypropylene, 3-hexyloxypropylene, 3-octyloxypropylene, 4-methoxybutylene, 4-ethoxybutylene, 4-propoxybutylene, 4-butoxybutylene, 4-hexyloxybutylene, 4-octyloxybutylene, 5-methoxypentylene, 5-propoxypentylene, 5-butoxypentylene, 5-pentyloxypentylene, 5-hexyloxypentylene, 5-octyloxypentylene, 6-methoxyhexylene, 6-ethoxyhexylene, 6-propoxyhexylene, 6-butoxyhexylene, 6-pentyloxyhexylene, 6-hexyloxypentylene, 6-octyloxyhexylene, 8-methoxyoctylene, 8-methoxyoctylene, 8-butoxyoctylene, 8-hexyloxyocytlene, 8-octyloxyoctylene and the like.

As used herein, the term "aryl" used alone or in combination is an aromatic ring containing 6–10 ring atoms and up to a total of 15 carbon atoms. The aromatic ring system includes unsubstituted as well as substituted phenyl, α-naphthyl and β-naphthyl. Moreover, as used herein, the Germ aryl also includes the alkyl substituted phenyl or alkyl substituted naphthyl groups. Examples include phenyl, tolyl, phenethyl, methylethyl, and the like. The preferred aryl group is phenyl or an alkyl substituted phenyl, such as tolyl.

The aryl groups used in the present invention may be unsubstituted or may be mono-, di- or tri-substituted. Such substituents include aryl groups, such as phenyl or tolyl; halogens, such as chlorine, bromine, fluorine or iodine; amino; nitro; hydroxy; alkyl containing 1–20 carbon atoms; alkoxy containing 1–10 carbon atoms, such as methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy, decyloxy, and the like; haloalkyl containing 1–8 carbon atoms and substituted by at least one halogen, such as, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromomethyl, 2,2-difluoroethyl, 3,3-dichloropropyl, 3,3-difluoropropyl, 4,4-dichlorobutyl, 4,4-difluorobutyl, trifluoromethyl, trichloromethyl, 2,2,2-trifluoroethyl, 2,3,3-trifluropropyl, 1,1,2,2-tetrafluoroethyl, 2,2,3,3-tetrafluoropropyl and the like; lower alkyl amino containing 1–10 carbon atoms; diloweralkylamino containing 1,10 carbon atoms, mercapto; thioalkyl containing 1–20 carbon atoms; aryloxy; arylalkoxy wherein the alkoxy groups contains 1–10 carbon atoms; and the like. The preferred substituted phenyl groups are phenyl, halogen, amino, nitro, hydroxy, alkyl, alkoxy, and haloalkyl. Moreover, it is preferred that the alkyl moiety in alkyl, alkoxy, and haloalkyl contain 1–6 carbon atoms and especially one carbon atom.

Arylalkyl, as used herein, is a bridging alkylene group containing 1–8 carbon atoms that is attached to an aryl group, as defined herein. The alkyl moiety in the aryl alkyl group may be straight chained or branched. Furthermore, the alkyl moiety may contain 1–20 carbon atoms, and more preferably 1–10 carbon atoms, and even more preferably 1–8 carbon atoms and most preferably 1–6 carbon atoms. Furthermore, the aryl alkyl group may be substituted wherein the substituents may be either on the alkyl group or on the aryl group. It is preferred that the substituents are on the aryl moiety. The aryl alkyl group may be mono, di, or tri-substituted and the preferred substituents are the same as those described hereinabove with respect to the phenyl group, e.g., aryl, halogen, amino, nitro, hydroxy, alkyl, alkoxy, haloalkyl, mercapto, thioalkyl, aryloxy, arylalkoxy and the like. Examples include benzyl, 2- phenylethyl, 1-phenylethyl, 3-phenylpropyl, 4-phenylbutyl, 5-phenylpentyl, 6-phenylhexyl, 8-phenyloctyl, naphthyl, 1-naphthylethyl, 2-naphthylethyl, 3-naphthylpropyl, 4-naphthylbutyl; 5-naphthylpentyl, 6-naphthyloctyl; and the like. It is preferred that the phenylalkyl group is unsubstituted.

The first step of the process of the present: invention utilizes an α-aryl-substituted aliphatic aldehyde of the formula:

Ar—CH₂—CH=O wherein Ar is as defined herein. Preferably Ar is phenyl, or phenyl substituted with at least one methyl or isobutyl or naphthyl or naphthyl substituted with at least one methoxy. The preferred Ar is 4-isobutylphenyl, 6-methoxy-2-naphthyl, 3-phenoxypropyl, 2'-fluoro-4-diphenyl, 4'-fluoro-4-diphenyl, 5-chloro-6-methoxy-2-naphthyl, 5-bromo-6-methoxy-2-naphthyl, 4-chlorophenyl, 4-difluoromethoxyphenyl, 6-hydroxy-2-naphthyl, or 5α-bromo-6-hydroxy-2-naphthyl.

This aromatic substituted aliphatic aldehyde is reacted with an optically active amine of the formula:

$$\begin{array}{c} R_1 \quad R_2 \\ C \\ NH_2 \quad H \end{array}$$

wherein $R_1$ and $R_2$ are defined herein. The reaction is usually run in an inert solvent, such as ether, tetrahydrofuran, and the like. This reaction can be effected at temperatures ranging from about $-25°$ C. to the reflux temperatures of the solvent, but more preferably ranging between $-10°$ to about $25°$ C. The preferred amines for use in this first step of the process of the present invention are those where $R_1$ is phenylalkyl or naphthylalkyl wherein the alkyl group has 1–4 carbon atoms or where $R_1$ is substituted phenylalkyl or naphthylalkyl wherein the aromatic nucleus is substituted with an alkyl group of 1–4 carbon atoms.

In the optically active amine disclosed in Formula II, an alkoxy moiety of $R_2$ is straight or branched chained having 1–6 carbon atoms and more preferably 1–4 carbon atoms and the alkyl group is a straight or branched chain having 1–6 carbon atoms and more preferably 1–14 carbon atoms. The most preferred $R_2$ groups are methoxymethylene or ethoxymethylene.

Both starting materials, i.e., the amine and aldehyde in the first step can be prepared by techniques known to one skilled in the art or are commercially available. For example, the starting aryl alkyl aldehyde can be prepared by oxidation of a primary alcohol, such as substituted benzyl alcohol or by oxidation of substituted aryl alkanes, such as ethanes with such oxidizing groups as a mixture of chromic acid and acetic anhydride or by chromyl chloride under Etard reaction conditions.

The product of step 1 of the present process is an aldimine having the formula:

$$\begin{array}{c} Ar \quad R_1 \quad R_2 \\ | \quad \quad C \\ C-CH=N \quad H \\ H \quad H \end{array} \quad V$$

wherein

Ar, $R_1$, and $R_2$ are as previously defined.

The aldimine of Formula V is preferably purified to remove any unreacted starting materials, solvents and by-products by conventional means known to one skilled in the art, such as distillation, phase separation or the like.

In the next step, the aldimine of Formula V is treated with a lithium base. Preferably, the base is a very strong base. More preferably, the conjugate acid of said base has a pKa relative to water of 16 or greater. Examples of the lithium bases include lithium salts containing the following bases:

$R_3CH_2O^\ominus$, $R_3CHCHO^\ominus$, $(R_3)_2CHO^\ominus$, $(R_3)_3CO^\ominus$, $R_3CONH^\ominus$, $R_3OOCCHR_4^\ominus$, $R_3CHCN^\ominus$, $HC\equiv C^\ominus$, $(Ar_1)_3C^\ominus$, $(Ar_1)_2CH^\ominus$, $H^\ominus$, $NH_2^\ominus$, $PhCH_2^\ominus$, $(CH_2 \ldots CH \ldots CH_2)^\ominus$, $Ph^\ominus$, $CH_2=CH^\ominus$, alkylide containing 1–6 carbon atoms such as $CH_3^\ominus$, $C_2H_5^\ominus$, $(CH_3)_3C^\ominus$, $(CH_3)_2CH^\ominus$, and the like, alkylamide, dialkylamide and the like;

wherein $R_3$ and $R_4$ are independently lower alkyl containing 1–6 carbon atoms, $Ar_1$ is an aryl group containing 6–10 carbon atoms, and Ph is phenyl.

A preferred lithium base is a lithium alkylamide having the formula:

$R_3NH^\ominus$ or $R_3R_4N^\ominus$ wherein $R_3$ and $R_4$ are as defined hereinabove.

As described hereinabove, the alkyl groups may be straight chained or branched. Examples include isopropylamide, diisopropylamide, methylamide, ethylamide, diethylamide, and the like. The preferred lithium base is lithium diisopropylamide.

The second step of the process may be run in an inert solvent which does not react with the reactants or with the product. Preferably, the inert solvent is volatile. Examples include diethylether and tetrahydrofuran. The preferred inert solvent is tetrahydrofuran. The reaction may be effected at temperatures ranging from about $-50°$ C. to the reflux temperatures, but it is preferred that the reaction is effected at temperatures ranging from between $-25°$ to about $10°$ C.

The product of reaction is a lithio-enamine having the following formula:

$$\left[\begin{array}{c} Ar \quad R_1 \quad H \\ | \quad \quad C \\ C=CH-N \quad R_2 \\ R \end{array}\right]^{1-1} \quad Li^+ \quad VI$$

Preferably, the lithio-enamine produced in this step is not further isolated but used directly in the next step. The reaction is also preferably run in the presence of molecular sieves or zeolites. Preferably 4.0–6.0 Å molecular sieves are used, but more preferably 4 Å molecular sieves. Furthermore, zeolites such as ZSM 5.5, can also be used in place of the molecular sieves.

In step III, the lithio-enamine produced is reacted with an alkyl halide, RX wherein R is alkyl, as defined herein and X is a halide. The preferred halides are bromo, chloro and especially iodo.

The product of the reaction with lithioenamine and alkyl halide is a compound of the formula:

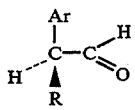

(VII)

Hydrolysis of this alkylated aldimine produces the aldehyde of Formula I. This hydrolysis can be done in the presence of acid, especially diluted acid, such as acetic acid, hydrochloric acid, sulfuric acid, and the like.

As a result of this process, the product formed is an optically active 2-aryl alkyl aldehyde.

It should be noted that the product formed in accordance with the process described hereinabove produces the aryl alkyl aldehyde in the S configuration.

It should be noted that the process of the present invention can yield the same optically active aldehyde by using slightly altered reactants. Thus, in the first step, an aliphatic aldehyde may be used as a starting material, i.e., a compound of the formula:

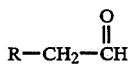

(VIII)

wherein R is as previously defined.

The compound of Formula VIII is then reacted with the same optically-active amine as above under the previously defined conditions, solvent and temperature to produce an aldimine of the formula:

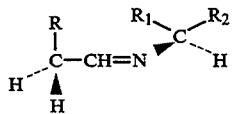

(IX)

wherein R, $R_1$, and $R_2$ are as previously defined. Subsequent treatment with a lithium base, as defined herein produces the lithio-enamine product which is then treated with an aryl halide of the formula:

wherein Ar and X are as previously defined. The preferred aryl halides are the aryl iodides. The product is then hydrolyzed as above to form the optically active aldehyde of Formula I.

The corresponding R aldehyde can be prepared using basically the same procedure. An aryl aldehyde, such as arylethanol, is condensed with optically active amine, followed by treatment with the lithium base to form the lithio enamines (preferably in the presence of 4.0 Å molecular sieves or ZSM-5.5 Å. However, instead of using an alkyl halide attack on the enamine, a substituted aryl halide, e.g., isobutyl-phenyliodide or 6-methoxy napthyl-2 iodide is used. Subsequent hydrolysis by acid lead directly to the corresponding R aldehyde. The enantiomeric aldehydes are oxidized to corresponding carboxylic acid using oxidizing agents described herein to form the corresponding R-carboxylic acid in high chemical yields and high optical purity.

The term "enantiomeric excess", ("ee") refers to the relative increase in the amount of one enantiomeric isomer produced by the present process relative to the other enantiomer. The convenient method of expressing the enantiomeric excess (ee) achieved by the process of the present invention, can be calculated by using the following equation $$ee = (E^1 - E^2)/(E^1 + E^2).$$

In the above equation, $E^1$ is the amount by weight of the first chiral form of the aldehyde or carboxylic acid that is present and $E^2$ is the amount of the second chiral form of the corresponding aldehyde or carboxylic acid. The extent of stereoselectivity (ee) is termed by methods known to one skilled in the art.

The process of the present invention can be used to prepare substantially pure 2-aryl alkyl aldehydes and the corresponding 2-aryl propionic acids in enantiomeric excess. It should be noted that the aldehydes formed by the present process can be readily oxidized to form the corresponding carboxylic acids without destroying the conformation of the α-carbon atom. Consequently, a variety of enantiomeric carboxylic acid compounds can be easily prepared by the process of the present invention by simply oxidizing the appropriate aldehydes precursors of Formula I with oxidizing agents known to one skilled in the art, such as sodium hypochlorite, chromic anhydride, and the like. Such profen type compounds also include the pharmaceutically acceptable esters or salts. Examples of the compounds prepared by the present invention are illustrated hereinbelow:

6-methoxy-2-naphthyl propionic acid;
3-phenoxyphenyl-2-propionic acid;
2'-fluoro-4-diphenyl-2-propionic acid;
4'-fluoro-diphenyl-2-propionic acid;
5-chloro-6-methoxy-2-methyl-2-propionic acid;
5-bromo-6-methoxy-2-naphthyl-2-propionic acid;
4-isobutylphenyl-2-propionic acid;
4-chlorophenyl-2-propionic acid;
3,5-difluoro-methoxy-phenyl-2-propionic acid and
6-hydroxy-2-methyl-2-propionic acid.

The preferred configuration about the alpha carbon is S-(+) in each of the above compounds.

The following examples given hereinbelow further illustrate the present invention.

EXAMPLE 1

PREPARATION OF
S-(−)-2-AMINO-1-METHOXY-3-PHENYLPROPANE

To a solution of 15.0 g (S)-phenyl-alaninal (≧0.099 mmol) in 100 ml of anhydrous $Et_2O$ of THF (DME, benzene-DME, benzene-DME 20/80 w/w), a suspension of potassium hydride (5.0 g=0.110 ml), dissolved in 100 ml THF, is being added dropwise under $N_2$-atmosphere at 20° C. The resulting yellow viscous mixture is allowed to stand for 8 hours. To this mixture, a solution of methyl iodide (n-alkyl-halide) of 15.0 g (≧0.09 mol) in 200 ml of THF is added dropwise over a time period of 2–3 hours, on standing for five hours at 20° C. The reaction mixture is poured into 2 liters of cold, saturated sodium chloride (aqueous) solution, extracted several times with $Et_2O$, dried over anhydrous $Na_2SO_4$, and then concentrated, yielding 21.2 g of crude product. Distillation at 0.05 mm Hg yields a product of 17.0 g clear oil (b.p. 53°–55° C.). The methoxy-(alkoxy) amine is dissolved in 500 ml of absolute EtOH, and dry HCl gas is bubbled through this solution for 15 minutes. The resulting solution is concentrated to-yield 20.0 g of a colorless solid (the hydrochloride), and can be recrystallized from EtOH/Et$_2$O (20:1); the solid has a melting point of m.p. 152°-153° C., $[\alpha]_{278}$(25° C.) +19.0° (C. 2.5 in EtOH), δ (D$_2$O) 2.90 (d, 2H), 3.34 (s, 3H), 3.54 (s, 2H), 3.59 (m, 1H) and 7.35 (broad, s, 5H). This compound can be stored at 20° C., preferably in a desiccator over NaOH. For preparation of the free methoxyamine (alkoxyamine), the hydrochloride is dissolved in 3% K$_2$CO$_3$ solution, and extracted with Et$_2$O, dried over anhydrous Na$_2$SO$_4$ and concentrated. Upon distillation at 50° C./0.05 mm Hg, a clear oil with $[\alpha]_{578}$(23° C.) −14.5° (c, 6.0 benzene) is obtained. NMR, CHCl$_3$: δ1.75 (broad s, 2H) which disappears upon addition of D$_2$O, 2.68 (m, 2H), 3.34 (broad, 6H), and 7.23 (s, 5H).

EXAMPLE 2

PREPARATION OF (S)-4-ISOBUTYLPHENYL-2-METHYLETHANAL 10 mmol of S-(−)-2-amino-1-methoxy-3-phenylpropane, dissolved in benzene prepared in accordance with the procedure described in Example 1 is placed into a flask containing 50 mL of THF. To the contents of the flask, 10 mmol of 2-(p-isobutylphenylbenzyl)aldehyde is added via a dropping funnel over a period of 10–15 minutes with continuous stirring at 0° C. After the addition of the aldehyde is complete, the solution is warmed to 20° C. over 2 hours and approximately 10 g Na$_2$SO$_4$ (anhydrous) is added, and after additional stirring for 30 minutes, the Na$_2$SO$_4$ is filtered off. The solvent is removed by distillation. The aldimine formed therefrom is distilled under reduced pressure or high vacuum at 0.05 mm Hg and yields 9.7–10 mmol of aldimine as a colorless liquid. These arylalkyl aldimines (substituted benzyl-aldimines) are dissolved in anhydrous THF and can be stored at −20° C. without deterioration.

Fresh diisopropylamine (2.00 ml, 14.3 mmol) is added under N$_2$ to 20 ml anhydrous THF, and the resulting solution cooled to 0°-4° C.

The butyl/lithium (5.0 ml, of a 2.5M solution in hexane or benzene) is slowly added to the aldimine with stirring at −25° C. for 30 minutes and then cooled to −50° C. to −70° C. The alkyl-halide, methyl-bromide or methyl-iodide (15 mmol) is dissolved in 10 ml of THF and added to this stirred mixture for 2 hours at −75° C. Upon warming to 20° C., and addition of 50 ml of Et$_2$O, the cloudy mixture is poured into 200 ml of cold water where the phases are separated. The alkylated aldimines are not purified any further. The crude alkylated aldimines are dissolved in 50 ml hexane and hydrolyzed by vigorous stirring for 15 minutes with aqueous acetic acid-sodium acetate solution at 20° C. The layers are separated, and the aqueous layer extracted with hexane again, the combined hexane layers are washed with water (20° C.), then 10% Na$_2$CO$_3$, again water and dried in vacuo. The evaporated hexane solution yields a crude yellow aldehyde as a viscous oil. Distillation at 75° C./0.005 mm Hg furnishes a clear and colorless S-aldehyde which by NMR methods and extrapolated specific rotation is 95% pure yield: 80% chemical yield, $[\alpha]_{578}$(23° C.) −10.1° (C., 2.0 n-hexane).

EXAMPLE 3

PREPARATION OF S-(+)-ISOBUTYLPHENYL-2-PROPIONIC ACID

A mixture of 10.0 g (0.056 mmol) of (S)-4-isobutylphenyl-1-methyl-ethanol, dissolved in 50 ml 1,4-dioxane is cooled to 0° C., and under continuous stirring and a cold solution (0° C.) of sodium hypochlorite in 200 ml of water is added through a dropping funnel. The stirring is continued for a further 20 minutes at 0° C. As soon as the reaction becomes vigorous, cooling to −5° C. is permitted and 500 ml of cold water is added. After the reaction hats subsided in approximately 20 min., the stirring is resumed and the reaction is continued until the temperature remains constant at 20° C. (1 hour). The solution is extracted with n-hexane, dried over magnesium sulfate (or 4.0 Å molecular sieves) and concentrated. Upon concentration, the S-(+)-4-isobutylphenyl-2-propionic acid crystallizes out. The crystals can be collected either by centrifugation (low speed) or filtration. Yield: 9.8 g S-(+) ibuprofen (85% chemical yield), $[\alpha]_D^{25}$+57°, 95%, Et$_2$O, m.p. 51° d. NMR(COCl$_3$), s 0.91 (d, J=7H, 6H), 1.50 (d, J=8 Hz, 3H), 7.01–7.32 (AA'BB',4H), 9.78 (br.s), 2.96 (1H).

EXAMPLE 4

LARGE SCALE PREPARATION OF S-(−)-2-AMINO-1-METHOXY-3-PHENYLPROPANE

A 20 liter continuous stirring tank reactor (CSTR) equipped with three inlets and one additional inlet for the addition of dry nitrogen (99.5% pure) and with a remote controlled stirring device, and a temperature controlled unit is used for the production of the above-identified compound. The CSTR can either be a glass or stainless steel reactor. The CSTR is filled with 15 liters of THF (or benzene) and 1.5 kg of S-phenyl-alaninal which is poured into the CSTR through one of the inlets with continuous stirring (250–300 rpm). The addition takes place under nitrogen so that the solution and the atmosphere in the CSTR is maintained under a dry atmosphere. During the addition of the S-phenyl, alaninal, the temperature is maintained at 20° C. Through a dropping funnel attached to the first inlet, 500 g of suspended potassium hydride in THF (benzene) (1 liter) is being added slowly over a period of time of 2 hours at 20° C. again with continuous stirring. The stirring is increased to 500–600 rpm for an additional two hours in order to complete the reaction. To the resulting pale solution, a solution of 1.5 kg of S-(−)-2-amino-1-methoxy-3-phenyl propane dissolved in two liters of THF is added slowly through a second inlet over a period of two hours at 20° C. and 500 rpm. The methoxy (alkoxy) amine is converted to the hydrochloride by adding dry HCl gas or a solution of 5 normal HCl in the dropping funnel through inlet 3 into the solution in the reaction vessel. The stirring speed is reduced to 300 rpm. The reaction vessel is cooled to 0°-5° C., and the S-(−)-2-amino-1-methoxy-3-phenyl propane can be recovered by filtering directly from the reactor, or by sack centrifugation, applying standard methods.

EXAMPLE 5

LARGE SCALE PREPARATION OF S-(−)-4-ISOBUTYL PHENYL-2-METHYL-ETHANAL (i) The appropriate aldimine as described herein is prepared in a 20 liter continuously stirred tank reactor (CSTR) containing 3 inlets equipped with a heater a remote controlled stirring device, and a remote temperature device and at least one of the inlets is furnished with a dropping funnel. The reaction vessel (CSTR) is purged with dry nitrogen and all the reactions described hereinbelow are conducted under nitrogen. The vessel is filled with 10 liters of hexane (or toluene or benzene) and the chiral alkoxy amine, (S)-(−)-2-amino-3-phenylpropane is added thereto (10 mmol) at 0°–5° C. The reaction is carried out at 0°–5° by adding 9.5–9.9 mol of para-isobutylbenzylaldehyde to the suspension with continuous stirring at 200 rpm. The reaction is completed within one hour. Upon warming the contents of the vessel by 15°–20° C., the solution is distilled off under vacuum (5–10 mm of mercury) through a condenser so that the reaction solvent can be recovered easily. Removal of the solvent leaves a pale yellow liquid in the vessel which does not need to be purified further.

(ii) The aryl-alkyl aldimine formed in (i) hereinabove can be dissolved in THF and stored at 20° C. without deleterious effects. It is not necessary to remove the hexane (or benzene) and the aldimine can be used to react directly with the aryl aldehyde.

When-ready for use, the aryl-alkyl aldimine is placed in the reaction vessel of the CSTR. A mixture of diisopropylamine (1.4 mmol) and butyl lithium (2.5M) in 2–4 liters of hexane (or benzene or toluene) is placed into a dropping funnel attached to inlet 2 of the reaction vessel under nitrogen. The other dropping funnel contains 1.5M methyl bromide. 500 g of activated molecular sieves, 4.0 Å or ZSM-5.5 are dispersed in the vessel under continuous stirring (200 rpm). The vessel is cooled down to −10° C., and then to −20° C. By reaching the appropriate temperature (−10° to −20° C.), both solutions from the dropping funnels (inlet 2 and inlet 1) are added simultaneously under continuous stirring into the solution containing the aryl alkyl aldimine. The reaction is completed within 45–60 minutes.

(iii) The alkyl halide to be used, e.g., (methyl bromide or methyl iodide or methyl chloride) is dissolved in 1 liter of THF and is added to the stirred mixture through one of the inlets. If Methyl chloride (1.5 mol) is used, it is also directly added through a suitable inlet from a methyl chloride tank into the vessel inlet. The stirring speed is also increased to 400 rpm if methyl chloride is used. The reaction is completed after one hour at −20° C. 5 liters of n-hexane is added through a dropping funnel and through another dropping funnel an aqueous solution of acetic acid/sodium acetate is added simultaneously therewith at 20° C. under continuous stirring (400–600 rpm). The S-aldehyde is in the n-hexane phase, which solvent is distilled off in accordance with the procedure as described in Example 4.

EXAMPLE 6

LARGE PREPARATION OF S-(+)-ISOBUTYLPHENYL-2-PROPIONIC ACID

Using the stirred tank reactor exemplified in Example 5, 1 kg of S-(−)-4-isobutylphenyl-1-methyl ethanal is dissolved in 5 liter of 1,4-dioctane. The vessel is cooled to 0° C. under continuous stirring (300 rpm); a cooled solution (0°–5° C.) of concentrated sodium hypochlorite in 2 l of water is added to a dropping funnel. The stirring is continued for at least 30 more minutes at 0° C. An endothermic reaction occurs so the temperature control of the reaction mixture in the vessel is critical. The reaction therefore is maintained between 0°–5° C. After 30 minutes, the reaction has subsided and the stirring is reduced to 200 rpm and the reaction is stirred continuously while the temperature remains constant at 20° C. for one hour. The solution is quenched with n-hexane or petroleum ether and dried over magnesium sulfate or 4.0 Å molecular sieves and concentrated. The work-up is in accordance with the procedure described in Example 2.

EXAMPLE 7

PREPARATION OF R-4-ISOBUTYL-2-METHYL-ETHANAL

The reactions described hereinbelow are all run under nitrogen. The aldimine is prepared from the reaction under $N_2$ of 10 mmol of the S-(−)-2-amino-2-methoxy-3-phenylpropane dissolved in THF or benzene and 10 mmol of freshly distilled arylaldehyde at 0° C. under continuous stirring. Upon warming to 20° C. for one to ten hours, 10 g of anhydrous sodium sulfate is added. After 30 minutes, the sodium sulfate is filtered off. The solvent is removed by distillation. The product therefrom, alkyl aldimine, is dissolved in anhydrous THF.

Diisopropylamine (15 mmol) is added to a separate vessel under nitrogen to 20 ml of anhydrous THF and the resulting solution is cooled to 0°–4° C. Zinc-lithium (5.0 ml of approximately 2.5M solution in n-hexane or benzene) is added with continuous stirring at 0° C. for 30 minutes and then cooled to −20° C. To the solution of the alkyl aldimine, the diisopropylamine/n-butyl lithium is added under $N_2$ at 20° C. over a period of time of 30 minutes and then cooled to −50° C. This solution is stirred in the presence of molecular sieves (4.0 Å) or ZSM 5.5 Å molecular sieve (activated) 200°–300 mg. Through a dropping funnel, 15 mmol of paraisobutylphenylbromide dissolved in 10 mL of THF is added and stirred for two hours at −20° C. The reaction is completed within 2 hours, and the mixture is warmed up to 20° C. 50 mL of ether is then added and the mixture is poured into 250 mL of cool water where the organic phase separates from the aqueous phase. The work-up is similar as that described in Example 2. The chemical yield is 80%, optical purity 95–98%; $[d]_{578}^{23} + 35.2°$ (C, 2.0 n-hexane).

The corresponding R-(−)-isobutylphenyl-2-propionic acid is prepared from the R-enantiomer of the aldehyde as described in Example 3.

The above preferred embodiments and examples are given to illustrate the scope and spirit of the present invention. These embodiments and examples will make apparent to those skilled in the art other embodiments and examples. These other embodiments and examples are within the contemplation of the present invention. Therefore the present invention should be limited only by the appended claims.

What is claimed is:

1. A process for preparing an optically active aldehyde in the S configuration of the formula:

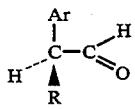

comprising
(a) condensing an α-aryl substituted aliphatic aldehyde of the formula Ar—$CH_2$—CH=O with an optically active amine in the S-configuration having the formula:

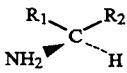

(b) treating the product of step (a) with a lithium containing base;
(c) reacting the product of step (b) with an alkyl halide and;
(d) hydrolyzing the product of step (c)
wherein
, Ar is aryl or substituted aryl;
R is alkyl;
$R_1$ is aryl, alkyl or substituted arylalkyl and
$R_2$ is alkoxyalkylene.

2. The process of claim 1 wherein the lithium containing base contains as the anionic moiety an ion of the formula:

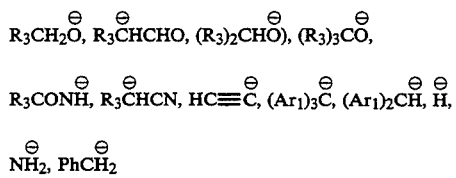

wherein $R_3$ and $R_4$ are independently lower alkyl containing 1–6 carbon atoms, Ar is an aryl group containing 6–10 carbon atoms, and Ph is phenyl.

3. The process of claim 1 wherein the lithium containing base contains as the anionic moiety an ion of the formula:

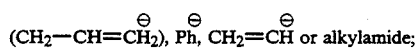

wherein $R_3$ and $R_4$ are independently an alkyl group containing 1–8 carbon atoms.

4. The process according to claim 3 wherein the base is diisopropylamide.

5. The process of claim 1 wherein molecular sieves are additionally present in step (b).

6. The process of claim 5 wherein the molecular sieves are 4.0 Å–6.0 Å molecular sieves.

7. The process of claim 6 wherein the molecular sieves are 4.0 Å molecular sieves.

8. The process according to claim 1 wherein zeolite is present in step (b).

9. The process according to claim 7 wherein the zeolite is 5.5-ZSM.

10. The process according to claim 9 wherein Ar is phenyl or naphthyl which may be unsubstituted or substituted with alkyl having 1–10 carbon atoms, halo, amino, alkoxy having 1–10 carbon atoms, halo alkyl containing 1–10 carbon atoms.

11. The process according to claim 1 wherein Ar is 4-isobutylphenyl, 6-methoxy-2-naphthyl, 3-phenoxypropyl, 2'-fluoro-4-diphenyl, 4'-fluoro-4-diphenyl, 5-chloro-6-methoxy-2-naphthyl, 5-bromo-6-methoxy-2-naphthyl, 4-chlorophenyl, 4-difluoromethoxyphenyl, 6-hydroxy-2-naphthyl, or 5-bromo-6-hydroxy-2-naphthyl.

12. The process according to claim 1 wherein $R_1$ is phenyl alkyl or substituted phenyl alkyl.

13. The process according to claim 1 wherein $R_1$ is phenyl alkyl which may be unsubstituted or substituted with halogen, amino, nitro, hydroxy, alkyl, alkoxy or haloalkyl.

14. The process according to claim 1 wherein $R_2$ is alkoxy alkylene having 1–6 carbon atoms.

15. The process according to claim 1 wherein $R_2$ is methoxymethylene or ethoxyethylene.

16. The process according to claim 1 wherein the alkyl halide is alkyl iodide.

17. A process for forming an optically active carboxylic acid in the S configuration of the formula:

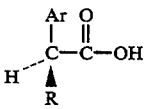

comprising
(a) condensing an α-aryl substituted aldehyde of the formula:

$$Ar-CH_2-CH=O$$

with an optically active amine in the S configuration having the formula:

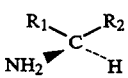

(b) treating the product of step (a) with a lithium containing base;
(c) reacting the product of step (b) with an alkyl halide;
(d) hydrolyzing the product of step (c) and
(e) oxidizing the product of step (d) with an oxidizing agent,
wherein
Ar is aryl or substituted aryl;
R is alkyl;
$R_1$ is arylalkyl or substituted arylalkyl and
$R_2$ is alkoxyalkylene.

18. The process according to claim 17 wherein the oxidizing agent is hypochlorite or chromic anhydride.

19. The process according to claim 17 wherein the product is S-ibuprofen or S-naproxen.

20. A process for preparing an optically active aldehyde in the S configuration of the formula:

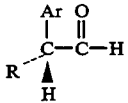

comprising:
(a) condensing an aldehyde of the formula:

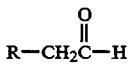

with an optically active amine of the formula

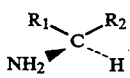

(b) treating the product of step (a) with a lithium containing base;
(c) reacting the product of step (b) with an aryl halide Ar—X and
(d) hydrolyzing the product of step (c), wherein
Ar is aryl or substituted aryl;
R is alkyl;
$R_1$ is arylalkyl or substituted arylalkyl,
X is halide; and
$R_2$ is alkoxyalkylene.

21. The process according to claim 20 wherein the lithium containing base contains on the anionic moiety an ion of the formula:

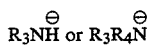

wherein $R_3$ and $R_4$ are independently an alkyl group containing 1–8 carbon atoms.

22. The process according to claim 21 wherein the lithium containing base is lithium diisopropylamide.

23. The process of claim 20 wherein molecular sieves or zeolite is additionally present in step (b).

24. The process according to claim 23 wherein 4.0 Å–6.0 Å molecular sieves are additionally present.

25. The process according to claim 23 wherein 4.0 Å molecular sieves or 5.5 ZSM is additionally present.

26. The process according to claim 21 wherein Ar is phenyl, naphthyl, substituted phenyl or substituted naphthyl wherein the substituents are aryl, halo, amino, nitro, hydroxy, alkyl having 1–10 carbon atoms, alkoxy having 1–10 carbon atoms or haloalkyl having 1–10 carbon atoms.

27. The process according to claim 20 wherein Ar is 4-isobutylphenyl, 6-methoxy-2-naphthyl, 3-phenoxypropyl, 2'-fluoro-4-diphenyl, 4'-fluoro-4-diphenyl, 5-chloro-6-methoxy-2-naphthyl, 5-bromo-6-methoxy-2-naphthyl, 4-chlorophenyl, 4-difluoromethoxyphenyl, 6-hydroxy-2-naphthyl, or 5-bromo-6-hydroxy-2-naphthyl.

28. The process according to claim 21 wherein $R_1$ is phenyl alkyl or substituted phenyl alkyl.

29. The process according to claim 21 wherein $R_1$ is phenyl alkyl which may be unsubstituted or substituted with halogen, amino, nitro, hydroxy, alkyl, alkoxy or haloalkyl.

30. The process according to claim 21 wherein $R_2$ is alkoxy alkylene having 1–6 carbon atoms.

31. The process according to claim 21 wherein $R_2$ is methoxymethylene or ethoxyethylene.

32. A process for forming an optically pure 2-aryl aldehyde in the R configuration having the formula:

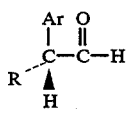

comprising
(a) condensing an α-aryl substituted aliphatic aldehyde of the formula Ar—CH₂—CH=O with an optically active amine in the S-configuration having the formula:

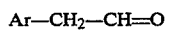

(b) treating the product of step (a) with a lithium containing base;
(c) reacting the product of step (b) with an aryl halide and
(d) hydrolyzing the product of step (b) wherein Ar is aryl or substituted aryl
R is alkyl;
$R_1$ is aryl alkyl or substituted arylalkyl and
$R_2$ is alkoxyalkylene.

33. The process of claim 32 wherein the aryl halide is an aryl iodide.

34. The process of claim 33 wherein the aryl iodide is isobutylphenyliodide or 6-methoxy naphthyl iodide.

35. A process for forming an optically active carboxylic acid in the R configuration having the formula

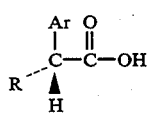

comprising
(a) condensing an α-aryl substituted aliphatic aldehyde of the formula Ar—CH₂—CH=O with an optically active amine in the S-configuration having the formula:

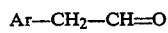

(b) treating the product of step (a) with a lithium containing base;
(c) reacting the product of step (b) with an aryl halide and
(d) hydrolyzing the product of step (b) wherein Ar is aryl or substituted aryl
R is alkyl;
$R_1$ is aryl alkyl or substituted arylalkyl
$R_2$ is alkoxyalkylene and
(e) oxidizing the product of step (d) with an oxidizing agent.

36. The process according to claim 35 wherein the oxidizing agent is hypochlorite or chromic acid.

37. A process for forming an optically active 2-aryl-propionic acid ester in the S configuration which comprises:
(a) condensing an α-aryl substituted aldehyde of the formula:

Ar—CH₂—CH=O with an optically active amine in the S configuration having the formula:

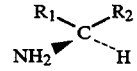

(b) treating the product of step (a) with a lithium containing base;

(c) reacting the product of step (b) with an alkyl halide;

(d) hydrolyzing the product of step (c):

(e) oxidizing the product of step (d) with an oxidizing agent and (f) reacting the product of step (e) with lower alcohol having 1–6 carbon atoms in the presence of acid, wherein Ar is aryl or substituted aryl, R is alkyl, $R_1$ is arylalkyl or substituted aryalkyl and $R_2$ is alkoxy alkylene.

* * * * *

UNITED STATES PATENT AND TRADEMARK OFFICE
CERTIFICATE OF CORRECTION

PATENT NO.   : 5,434,302
DATED        : July 18, 1995
INVENTOR(S)  : H. Henrich Paradies It is certified that error appears in the above-indentified patent and that said Letters Patent is hereby corrected as shown below:

```
Column 1, line 16:  after "formed"  insert --by--
Column 1, line 32:  "Hurt"  should read --Hutt--
Column 1, line 42:  "Senantiomer"  should read
--S-enantiomer--
Column 2, line 3:   "670"  should read --7670--
Column 4, line 6:   "Germ"  should read --term--
Column 4, line 33:  "1,10"  should read --1-10--
Column 5, line 36:  "1-14"  should read --1-4--
Column 8, line 67:  "to-yield"  should read
--to yield--
```

Signed and Sealed this

Ninth Day of April, 1996

Attest:

BRUCE LEHMAN

*Attesting Officer*   *Commissioner of Patents and Trademarks*